United States Patent
Resch et al.

(10) Patent No.: US 6,673,115 B2
(45) Date of Patent: Jan. 6, 2004

(54) ANATOMIC GLENOID SHOULDER PROSTHESIS TOGETHER WITH METHODS AND TOOLS FOR IMPLANTING SAME

(75) Inventors: Herbert Resch, Salzburg-Aigen (AT); Damon Servidio, Montville, NJ (US); Peter Nuijten, Limerick (IE)

(73) Assignee: Stryker Technologies Corporation, Kalamazoo, MI (US)

( * ) Notice: Subject to any disclaimer, the term of this patent is extended or adjusted under 35 U.S.C. 154(b) by 40 days.

(21) Appl. No.: 10/059,617

(22) Filed: Jan. 29, 2002

(65) Prior Publication Data

US 2002/0082702 A1 Jun. 27, 2002

Related U.S. Application Data

(62) Division of application No. 08/926,358, filed on Sep. 9, 1997, now Pat. No. 6,379,386.

(51) Int. Cl.[7] .................................................. A61F 2/40
(52) U.S. Cl. ..................... 623/19.13; 606/96; 606/86; 606/79
(58) Field of Search .............................. 606/53, 54, 59, 606/60, 72, 73, 79, 80, 86, 96, 99, 102, 104; 623/16, 18, 19

(56) References Cited

U.S. PATENT DOCUMENTS

| 4,021,864 A | 5/1977 | Waugh |
| 4,106,130 A | 8/1978 | Scales |
| 4,307,473 A | 12/1981 | Weber |
| 4,470,158 A | 9/1984 | Pappas et al. |
| 4,550,450 A | 11/1985 | Kinnett |
| D285,968 S | 9/1986 | Kinnett |
| 4,986,833 A | 1/1991 | Worland |
| 5,074,880 A | 12/1991 | Mansat |
| 5,080,673 A | 1/1992 | Burkhead et al. |
| 5,405,401 A | 4/1995 | Lippincott, III et al. |
| 5,593,448 A | 1/1997 | Dong |
| 5,658,347 A | 8/1997 | Sarkisian et al. |
| 5,674,288 A | 10/1997 | Knapp et al. |
| 5,702,469 A | 12/1997 | Whipple et al. |
| 5,702,470 A | 12/1997 | Menon |
| 5,800,551 A | 9/1998 | Williamson et al. |

FOREIGN PATENT DOCUMENTS

FR 2 579 454 10/1986

*Primary Examiner*—Cary E. O'Connor
*Assistant Examiner*—Candice C. Melson
(74) *Attorney, Agent, or Firm*—Lerner, David, Littenberg, Krumholz & Mentlik, LLP

(57) ABSTRACT

A glenoid component includes an oval body having a concave lateral articulating surface and an opposing medial surface with a keel extending from the medial surface. The keel extends along a line which is anteriorly offset from the center line of the concave surface and is not collinear with any radius of the concave surface. New methods and tools are provided for the implantation of the glenoid component. Sizer drill guides are provided with an alignment arm which assures that the anterior/posterior angle of the pilot hole is approximately 65 degrees. An improved reamer tool is provided which allows the practitioner to attach a reamer head of selected size to the reamer rather than choosing among several reamers of different size at the time of the procedure. A new keel drill guide is provided which locates three drill guide holes in a plane which is offset approximately 2 mm anterior of the pilot hole. A new broach tool is provided for connecting the three holes and form a triangular or trapezoidal cavity for the keel. Methods for installing the glenoid component and using the tools are also disclosed.

28 Claims, 7 Drawing Sheets

ANATOMIC GLENOID SHOULDER PROSTHESIS TOGETHER WITH METHODS AND TOOLS FOR IMPLANTING SAME

CROSS-REFERENCE TO RELATED APPLICATIONS

This application is a divisional of U.S. Ser. No. 08/926,358 filed Sep. 9, 1997 now U.S. Pat. No. 6,379,386.

BACKGROUND OF THE INVENTION

The invention relates to a glenoid component for a shoulder prosthesis. More particularly, the invention relates to a glenoid component having a long off-axis keel and methods and tools for implanting the glenoid component.

The human shoulder joint includes two major components, the glenoid component and the humeral component. The glenoid component is the portion of the scapula which forms a socket-like structure for the humeral component. The humeral component is the upper end of the upper arm which forms a ball-like structure which fits into the glenoid component.

Prosthetic shoulder joints are well known in the art and many different glenoid and humeral components have been provided. Various methods and tools have also been provided for implanting a prosthetic glenoid component. A typical state-of-the-art glenoid component is disclosed in U.S. Pat. No. 5,489,310 to Mikhail which also discloses methods and tools for implanting the component.

The typical glenoid component includes a circular body having a concave lateral articulating surface and an opposing medial surface with a stem extending along a central axis from the medial surface. The glenoid component is installed after the scapula is resected to remove the natural glenoid and a cavity is formed in the neck of the scapula to receive the prosthetic glenoid component.

The methods and tools described in the '310 patent are designed to permit installation of the glenoid component with a minimal amount of bone removal required in the preparation of the scapula. Utilizing the methods and tools of the '310 patent, different sizer guides are used to measure the size of the natural glenoid cavity in order to choose a prosthetic component of proper size through trial and error. The sizer guides each have a plurality of pointed members and a central hole. After the proper size has been determined, the corresponding sizer guide is hammered into the bone of the scapula and the central hole in the sizer guide is used as a drill guide to drill a 15–30 mm hole in the scapula.

A reamer of appropriate size is then chosen based on the size of the sizer guide previously chosen. The reamer has a symmetrical head with a plurality of tapered cutting blades and a peripheral stop surface. The previously drilled hole is used as a center guide for the reamer. The reamer is used to create a cavity in the scapula in which the prosthetic glenoid component will be installed. After the cavity has been created, the circular glenoid component is installed in the cavity, with or without the use of bone cement.

Despite the numerous advances in the designs of glenoid components and the methods and tools used for their installation, these prostheses still lack the stability and strength of natural healthy glenoid components and the relative positions of the prosthetic glenoid and humeral components most often does not provide the proper soft tissue balance.

SUMMARY OF THE INVENTION

It is therefore an object of the invention to provide a prosthetic glenoid component which more accurately copies the function of a natural glenoid component.

It is also an object of the invention to provide prosthetic glenoid component which is more stable than existing prosthetic glenoid components.

It is another object of the invention to provide a prosthetic glenoid component which, when implanted, provides proper soft tissue balance between the glenoid component and the humeral component.

It is still another object of the invention to provide a glenoid component and methods and tools for its installation which achieve the aforementioned objects and which minimize the risk of damage to the posterior scapula.

In accord with these objects which will be discussed in detail below, the glenoid component of the present invention includes an oval body having a concave lateral articulating surface and an opposing medial surface with a keel extending from the medial surface.

According to one aspect of the invention, the keel extends along a line which is anteriorly offset from the center line of the concave surface and is not collinear with any radius of the concave surface.

According to another aspect of the invention, the keel is substantially triangular or trapezoidal in shape and functions like an I-beam to provide greater support for the glenoid component when attached to the scapula.

According to a presently preferred embodiment, the medial surface of the glenoid component has ridges and the keel has a central hole, both of which enhance fixation of the component to the scapula.

The design of the glenoid component of the invention is based in part on the observation that the centerline of a natural glenoid component is not collinear with the centerline of scapula bone mass. It was thus hypothesized that the symmetrical glenoid components with central stems and the methods and tools for their installation result in the affixation of the component to a portion of the scapula which has reduced bone mass. It is believed that this is the cause of reduced stability, damage to the posterior scapula, and imbalance in the soft tissues between the glenoid and humeral components.

According to further aspects of the invention, new methods and tools are provided for the implantation of the novel glenoid component. In particular, sizer drill guides are provided with an additional alignment arm which assures that the anterior/posterior angle of the pilot hole is approximately 65 degrees. This angle was discovered to be the optimal angle in a series of unpublished cadaver studies.

According to other aspects of the invention, an improved reamer tool is provided which allows the practitioner to attach a reamer head of selected size to the reamer rather than choosing among several reamers of different size at the time of the procedure.

In order to provide the proper hole in the scapula for the keel of the glenoid, a new keel drill guide is provided which locates three drill guide holes in a plane which is offset approximately 2 mm anterior of the pilot hole. One of the drill guide holes is a central hole and the other two holes parallel therewith. A new broach tool is provided for connecting the three holes and forming a triangular cavity for the keel.

The methods of installation according to the invention include selecting the appropriate sizer drill guide in a conventional way, using the sizer drill guide of the invention to drill a pilot hole in the center of the glenoid, but with an A/P angle of approximately 65 degrees, using the new glenoid reamer to resect the glenoid cavity around the pilot hole, using the new keel drill guide to drill three holes which have axes aligned in a plane which is anteriorly offset from the pilot holes, and using broach tool to connect the three holes and form a triangular cavity for the keel. The glenoid component is then installed with bone cement and is placed to tilt slightly downward (up to approximately 5 degrees) in order to reduce superior migration of the humeral head.

Additional objects and advantages of this invention will be become apparent to those skilled in the art upon reference to the detailed description taken in conjunction with the provided figures.

DETAILED DESCRIPTION

Figure 2:
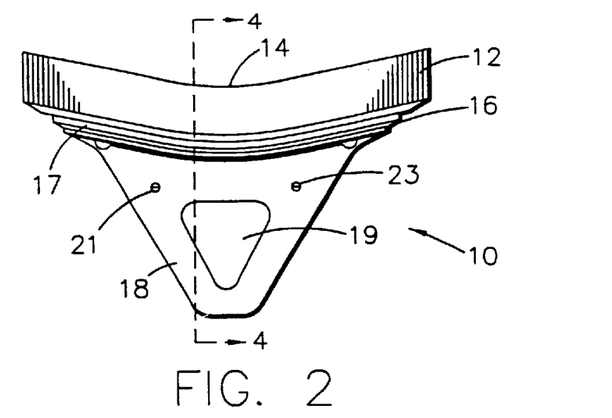
FIG. 2 is a posterior side elevational view of the glenoid component of FIG. 1.
Figure 3:
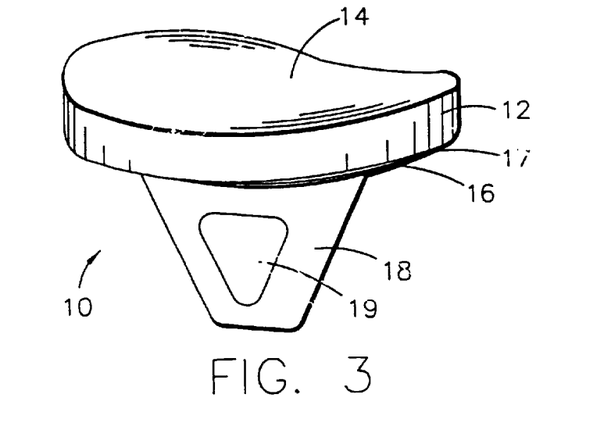
FIG. 3 is a perspective view of the glenoid component of FIG. 1.
Figure 4:
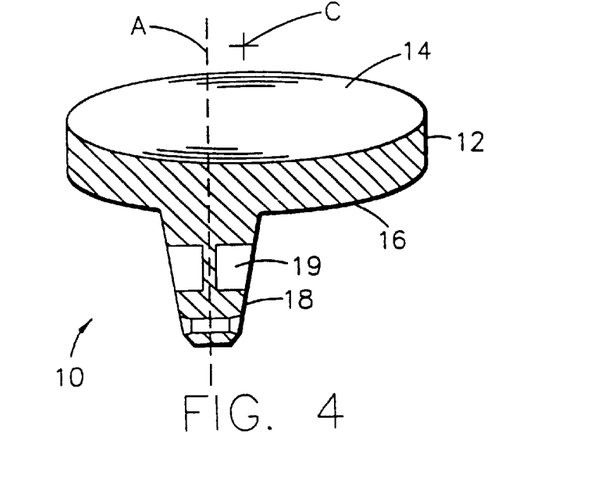
FIG. 4 is a cross section taken along line 4—4 in FIG. 2.
Figure 5:
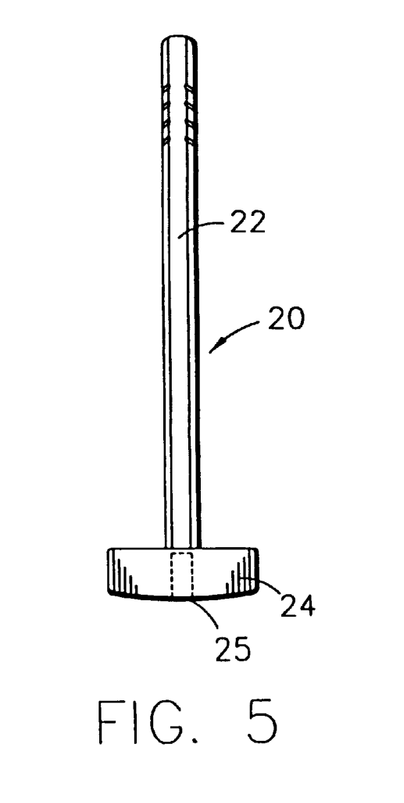
FIG. 5 is a posterior side elevational view of a component of the pilot guide according to the invention.
Figures 6, 7:
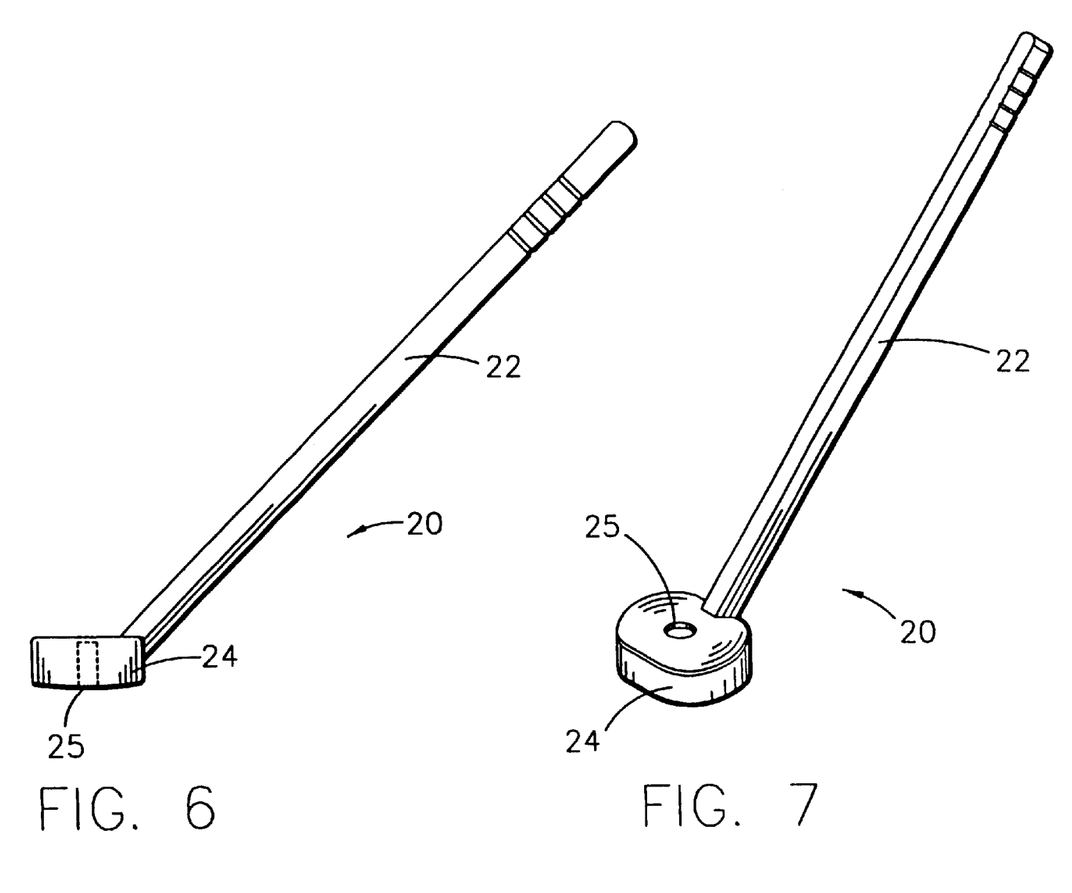
FIG. 6 is a (superior or inferior) side elevational view of the component of FIG. 5.
FIG. 7 is a perspective view of the component of FIGS. 5 and 6.

Referring now to FIGS. 1 through 4, a glenoid component 10 according to the invention includes an oval body 12 having a concave lateral articulating surface 14 and an opposing medial surface 16 with a keel 18 extending from the medial surface 16. According to one aspect of the invention, and as shown best in FIGS. 1 and 4, the keel 18 extends along a line "A" which is anteriorly offset from the center line "B" of the concave surface and is not collinear with any radius of the concave surface. For example, as shown in FIG. 4, the line "A", along which the keel 18 extends, does not intersect the center "C", from which the surface 14 is generated.

The prosthetic glenoid component has a body having a concave lateral surface and an opposed medial surface with a keel extending from the medial surface. The concave lateral surface being defined by one or more radii. The keel lies in a plane which is anteriorly offset from the center of said body and said plane lying non-collinear relative to each of the one or more radii.

Figure 1:
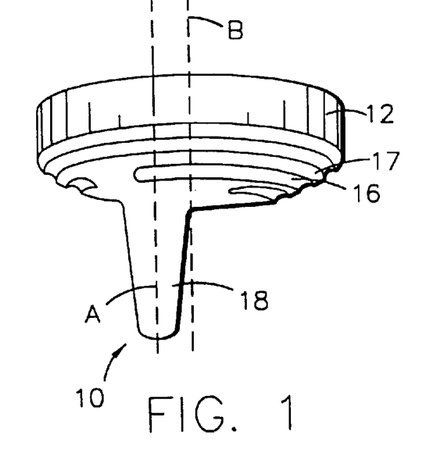
FIG. 1 is a superior-posterior side elevational view of a glenoid component according to the invention.

According to a presently preferred embodiment, the keel 18 is substantially triangular or trapezoidal in shape. The superior and inferior sides of the keel 18 taper substantially as shown in FIGS. 2 and 3. However, the anterior and posterior sides of the keel 18 also taper as shown in FIGS. 1 and 4. This design of the keel allows it to function like an I-beam to provide greater support for the glenoid component when attached to the scapula.

According to a presently preferred embodiment, the medial surface 16 of the glenoid component has ridges, e.g. 17, and the keel has a recessed pocket 19, both of which enhance fixation of the component to the scapula.

As seen in FIG. 2, the keel 18 is also advantageously provided with a pair of small holes 21, 23 which are dimensioned to receive a radiopaque material such as radiopaque wires. The location of these holes relative to the geometry of the glenoid component 10 permits fluroscopic examination of the superior-inferior version of the component during implantation. In other words, the location of the holes defines an axis which is parallel to the vertical axis of the component. Those skilled in the art will appreciate that the glenoid component is made in a variety of sizes for use with large and small patients. The relative overall dimensions of the component can be given for example as approximately 1.299 in the superior-inferior direction, approximately 0.945 in the anterior-posterior direction, and approximately 0.750 in the medial-lateral direction.

Referring now to FIGS. 5–9, a sizer drill guide 20 according to the invention includes handle portion 22 and a template head 24. The head and the handle are attached to each other at an angle of approximately 45 degrees such that when the drill guide 20 is in use, the handle extends anteriorly from the head. The head 24 has a central hole 25 which is dimensioned to receive a drill bit 26 (FIGS. 8 and 9) for drilling a pilot hole in the glenoid, prior to reaming.

Those skilled in the art will appreciate that the size of the head 24 is designed to correspond to the size of a glenoid component. Thus, as described in more detail below, the practitioner will use a number of sizer drill guides until the appropriate size is found.

Figure 8:
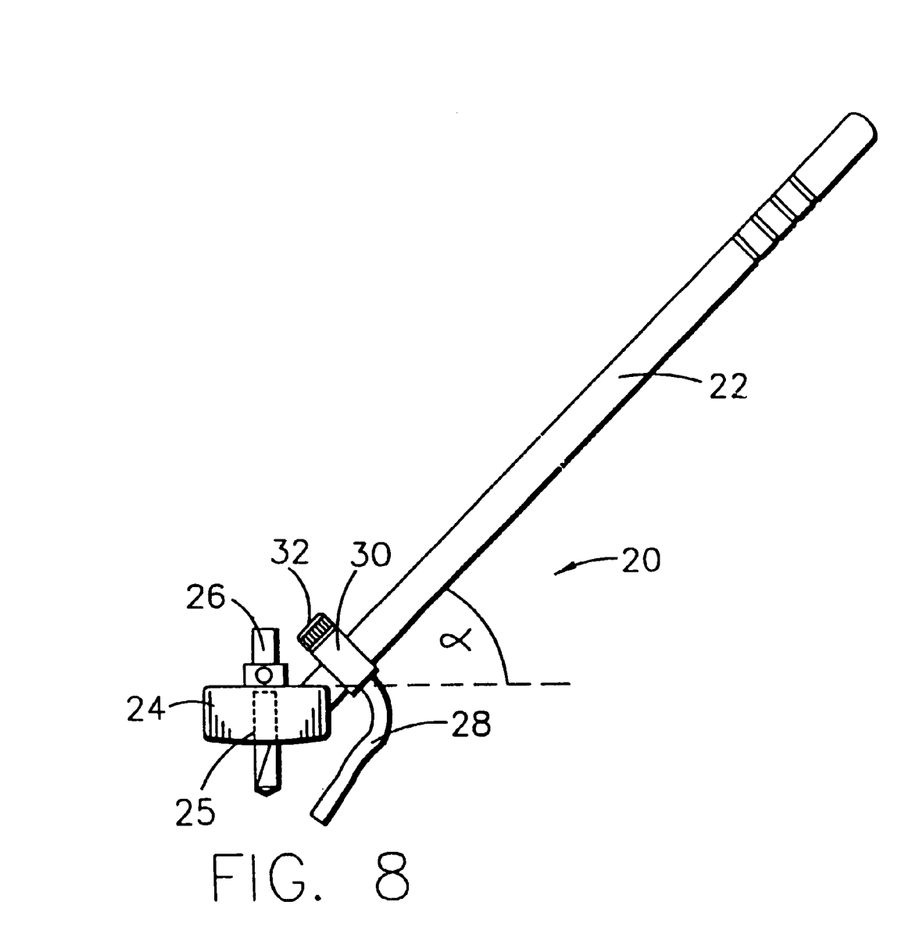
FIG. 8 is a (superior or inferior) side elevational view of the component of FIGS. 5–7 with the alignment arm according to the invention attached to the component and showing the location of the pilot hole drill bit.
Figure 9:
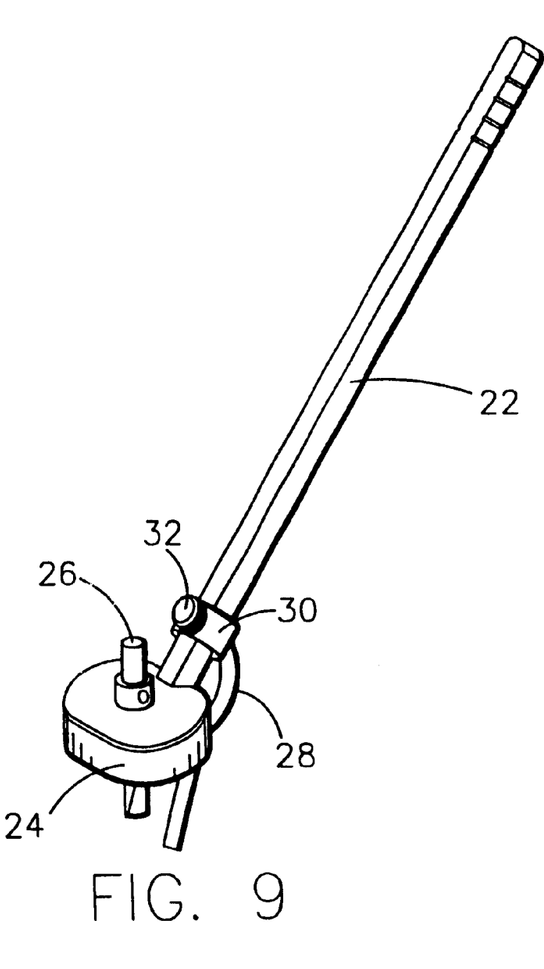
FIG. 9 is a perspective view of the assembly of FIG. 8.

According to the invention, the sizer drill guides are provided with an alignment arm 28 which assures that the anterior/posterior angle a of the pilot hole is approximately 65 degrees.

According to a presently preferred embodiment, the arm 28 is removably attached to the handle 22 by a collar 30 and a set screw 32. In use, the arm is placed against the anterior scapula and this automatically angles the drill guide at 65 degrees.

Turning now to FIGS. 10–14, an improved reamer according to the invention includes a handle 40 with an angled head 42. The handle includes a drive shaft 44 which has a proximal coupling 46 for coupling it to a motor (not shown). The drive shaft is coupled at its distal end to a rotating tip 48. The tip 48 has a rounded distal end 50 and an intermediate threaded portion 52. A removable reaming tool 54 is a generally circular member having a central threaded bore 56, a reaming surface 58, and a plurality of angularly spaced apart through slots 60a–60f. The reaming tool 54 is made in a variety of sizes, each of which corresponds to a different size glenoid component. However, each of the reaming tools has the same sized central threaded bore 56 so that it may be attached to the threaded portion 52 of the tip 48 of the reamer handle 40.

According to the presently preferred embodiment, the reaming tools 54 each have six through slots which are evenly spaced apart. These slots serve two functions, to allow through passage of bone tissue as the glenoid is being reamed, and to permit the rapid attachment of the tool 54 to the tip 48 using a special tool 62, shown in FIG. 14. The tool 62 has three slot engaging members 64a, 64c, 64e which extend downwardly from a circular base 66 and an upstanding T-handle 68 which extends from the other side of the base 66. The slot engaging members are dimensioned and angularly spaced apart to engage three of the six through slots in the tool 54.

Figures 10, 13, 14:
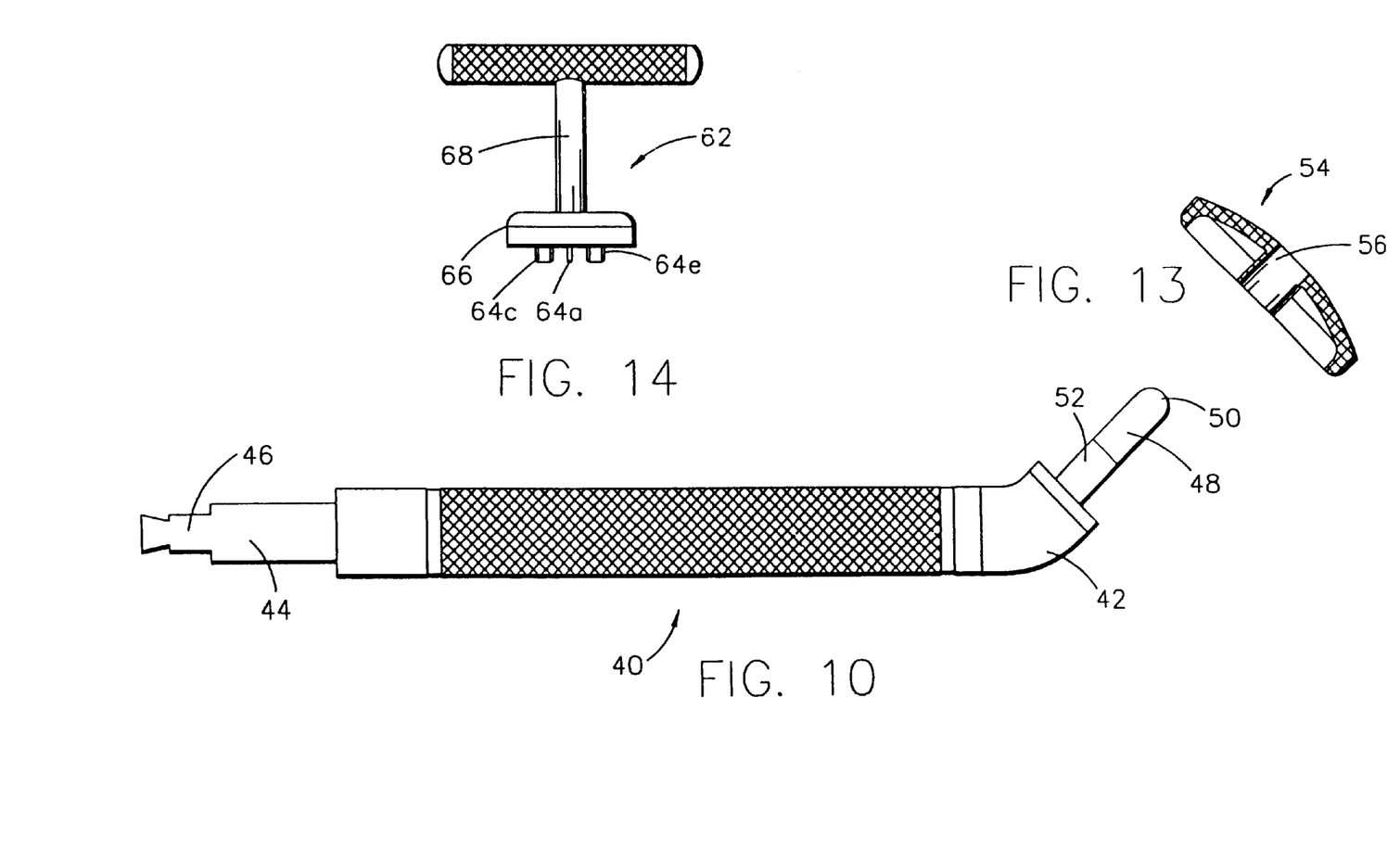
FIG. 10 is a side elevational view of a reamer handle according to the invention.
FIG. 13 is a cross section taken along line 13—13 in FIG. 12.
FIG. 14 is a side elevational view of a tool for removably attaching the reamer head to the handle according to the invention.
Figure 11:
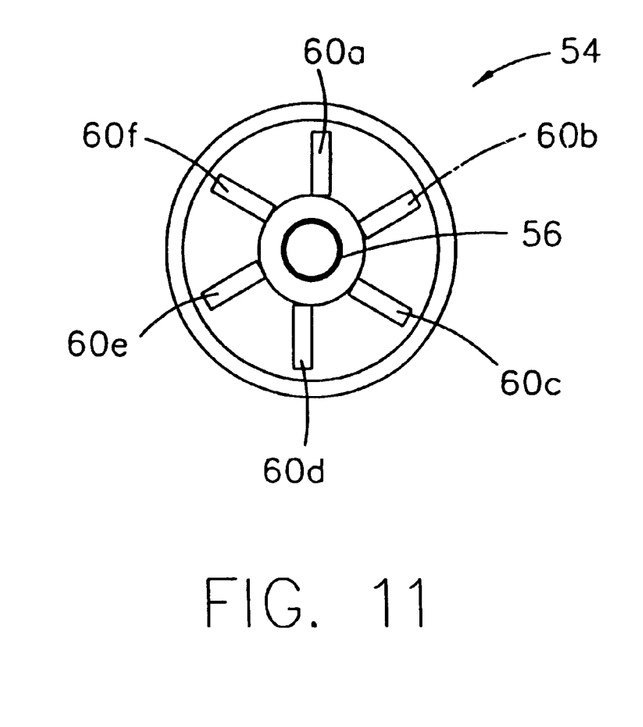
FIG. 11 is a back side view of a reamer head according to the invention.
Figure 12:
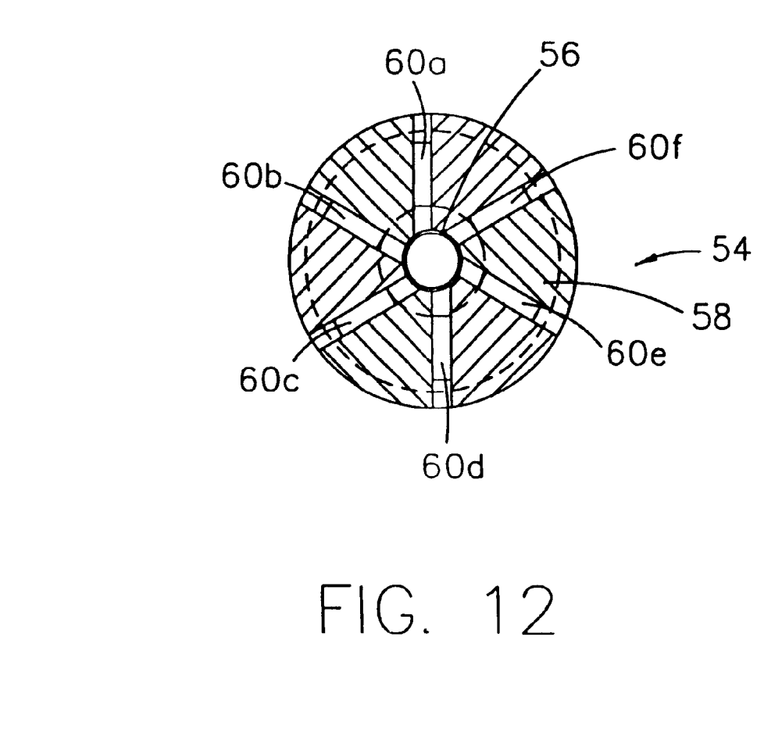
FIG. 12 is a front side view of the reamer head of FIG. 11.

Those skilled in the art will appreciate therefore, that the tool 54 is attached to the tip 48 by placing the threaded hole 56 over the tip 48 and spinning the tool 54 until the threads in the bore 56 engage the threads 52 on the tip 48. When the reaming tool 54 is so engaged, the tightening tool 62 is used to tighten the reaming tool 54 to the tip 48.

It will also be appreciated that the smooth end 50 of the tip 48 will extend beyond the surface 58 of the reaming tool 54. This portion of the tip will be used to locate the reamer relative to the pilot hole as described in more detail below.

Figure 15:
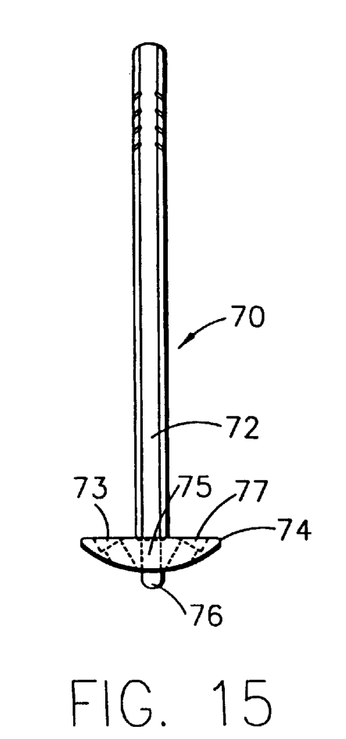
FIG. 15 is a posterior side elevational view of the keel drill guide according to the invention.
Figures 16, 17:
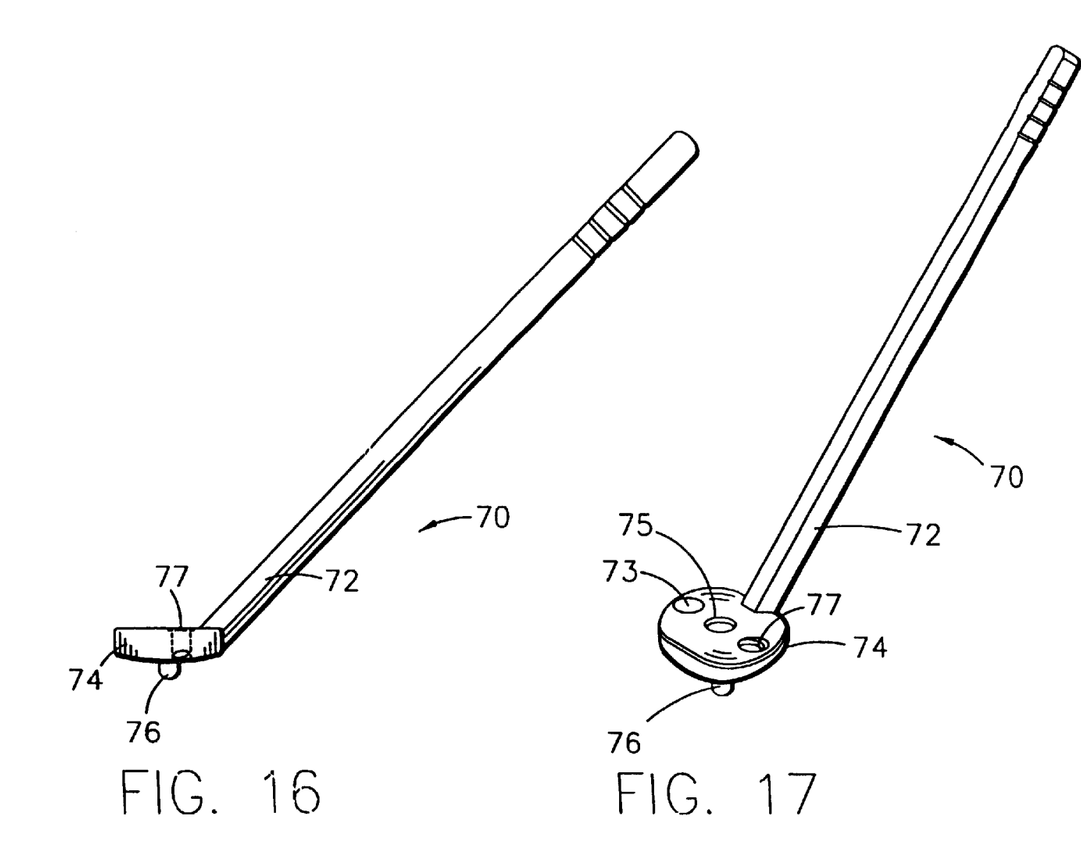
FIG. 16 is a (superior or inferior) side elevational view of the drill guide of FIG. 15.
FIG. 17 is a perspective view of the drill guide of FIGS. 15 and 16.

Turning now to FIGS. 15–17, a keel drill guide 70 according to the invention includes a handle portion 72 and a drill template head 74. The template head 74 has a distally extending central guide post 76 and three holes 73, 75, 77 for receiving drill bits as described in more detail below. The overall size and shape of the template head 74 corresponds to the overall size and shape of the template head 24 of the sizer drill guide 20 described above.

Thus, it will be appreciated that the keel drill guide 70 is provided in different sizes corresponding to the different size glenoid components. The central guide post 76 is dimensioned to fit inside the pilot hole created with the sizer drill guide and the three holes 73, 75, 77 are arranged with their axes lying in a plane which is spaced apart from the axis of the guide post 76.

More particularly, as seen best in FIG. 16, the axes of the holes lie in a plane which is anteriorly spaced apart from the guide post 76. Those skilled in the art will appreciate that the anterior offset of the holes corresponds to the anterior offset (approximately 2 mm) of the keel in the glenoid component. As seen best in FIG. 15, the axes of the two outer holes 73, 77 are angled relative to the middle hole 75.

It will be appreciated that after three holes in the scapula are drilled with the aid of the keel drill guide, the three holes will approximate the triangular hole required to receive the keel of the glenoid component. The walls between the three holes are cut with the aid of the broach tool, described below with references to FIGS. 18 and 19 to form a triangular or trapezoidal cavity for the keel.

Figures 18, 19:
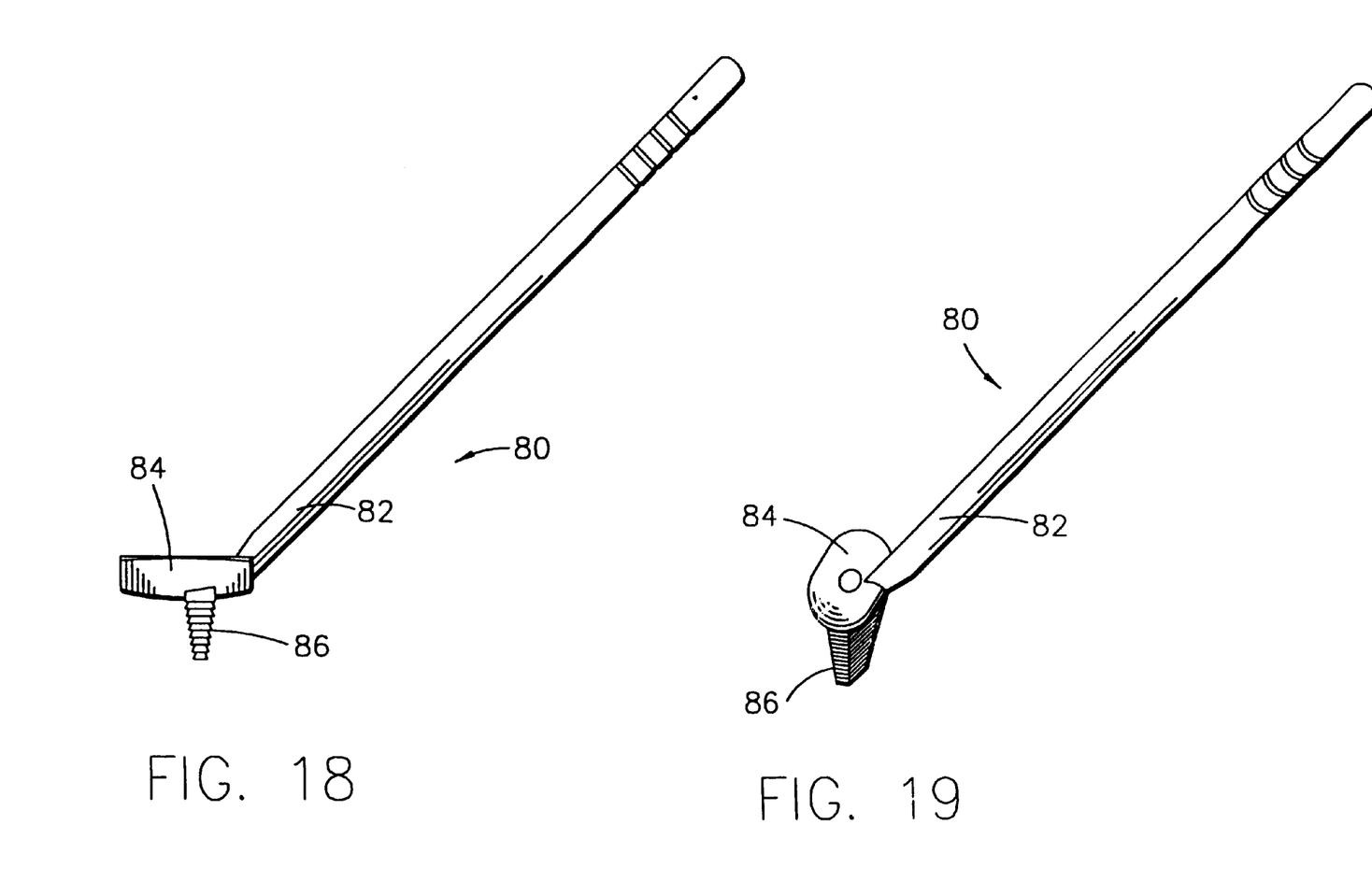
FIG. 18 is a (superior or inferior) side elevational view of keel hole broach according to the invention.
FIG. 19 is a perspective view of the broach of FIG. 18.

As shown in FIGS. 18 and 19, a broach tool 80 according to the invention includes a handle portion 82, a base portion 84, and a rasp 86 which extends downward from the base portion. The base portion is dimensioned to match the template portions of the drill guides 20 and 70 described above. Thus the broach tool 80 is provided in different sizes which correspond to the different size glenoid components. The rasp 86 is located and dimensioned to correspond to the keel of the corresponding glenoid component. Those skilled in the art will appreciate that the broach tool 80 is utilized by inserting the rasp into the middle hole created with the keel drill guide 70 and cuts through the wall of the middle hole into the side angled holes.

Referring now to all of the figures, the methods of implanting the glenoid component according to the invention include selecting the appropriate sizer drill guide (FIGS. 5–9) in a conventional way and using the sizer drill guide of the invention to drill a pilot hole in the center of the glenoid with an A/P angle of approximately 65 degrees. The drill guide should be in firm contact with the glenoid surface and neck. In cases of severe anterior-posterior version (pathological retro- or anteversion) some bone may need to be removed from either the anterior or posterior side of the glenoid with a high speed burr. The 65 degree angle and the use of a drill bit with a stop assures that the pilot hole does not perforate the anterior or posterior cortex.

Having selected a particular size for the drill guide shown in FIGS. 5–9, corresponding sizes will be used in the following steps. In particular, a corresponding size reamer tool (FIGS. 11, 12 and 13) is selected and attached to the reamer handle (FIG. 10) using the special tool (FIG. 14). The rounded tip 50 (FIG. 10) is then located in the pilot hole and the glenoid is symmetrically reamed surrounding the pilot hole. Because the glenoid component of the invention is longer in the superior-inferior direction than in the anterior posterior-direction, and because the reamer is circular, a superior portion of the glenoid is removed with a high speed burr after the reaming step is completed.

A correspondingly sized drill guide (FIGS. 15–17) is then chosen. The guide post 76 is placed in the pilot hole and the guide holes 73, 75, 77 are used to drill three holes which have axes aligned in a plane which is anteriorly offset from the pilot hole. A correspondingly sized broach tool (FIGS. 18 and 19) is then chosen and is used to connect the three holes and form a triangular or trapezoidal cavity for the keel. A correspondingly sized glenoid component (FIGS. 1–4) is then installed with bone cement covering the keel and the medial surface and is placed to tilt slightly downward (up to approximately 5 degrees) in order to reduce superior migration of the humeral head. The angular alignment of the glenoid component may be facilitated by using radiopaque material (such as radiopaque wire(s)) in the two small holes in the keel and viewing placement fluoroscopically.

There have been described and illustrated herein a glenoid component and methods and apparatus for implanting the glenoid component. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of implanting a prosthetic glenoid component in a scapula, the glenoid component having a medially extending keel which is anteriorly offset from the center of the glenoid component, said method comprising:

selecting an appropriately sized drill guide having a drill template which approximates the size of the glenoid component to be implanted and having a central through bore for locating a pilot hole in the scapula;

placing the drill template against the glenoid surface of the scapula;

drilling through the through bore of the drill template to form a pilot hole in the scapula;

selecting an appropriately sized reaming tool having a reaming surface which approximates the size of the glenoid component to be implanted and having a central guide pin dimensioned to fit in the pilot hole;

locating the guide pin in the pilot hole;

creating a recess in the glenoid surface of the scapula with the reaming tool;

selecting an appropriately sized keel drill guide having a drill template which approximates the size of the glenoid component to be implanted and having a through bore which is anteriorly offset from the center of the drill template;

placing the keel drill template against the recess in the glenoid surface of the scapula;

drilling through the keel drill guide drill template to form a keel receiving hole which is anteriorly offset from the center of the recess in the glenoid surface of the scapulas;

implanting the prosthetic glenoid component in the scapula.

2. The method according to claim 1, wherein said step of selecting an appropriately sized drill guide further comprises the step of selecting a drill guide having an alignment arm for automatically aligning the angle of the through hole relative to the scapula.

3. The method according to claim 1, wherein said step of selecting an appropriately sized drill guide further comprises the step of selecting a drill guide having an alignment arm for automatically aligning the through hole relative to the scapula at an angle of approximately 65 degrees; and said step of drilling through the through bore of the drill template to form a pilot hole in the scapula further comprises the step of forming a pilot hole which has an angle of approximately 65 degrees relative to the scapula.

4. The method according to claim 1, wherein said step of selecting an appropriately sized reaming tool having a reaming surface which approximates the size of the glenoid component to be implanted and having a central guide pin dimensioned to fit in the pilot hole further comprises the step of selecting an appropriately sized reaming head having a threaded central through bore and attaching the reaming head to a reaming tool having a threaded shaft.

5. The method according to claim 1 further comprising the steps of:
after said step of drilling through the keel drill guide drill template, selecting an appropriately sized broach tool having a rasp which approximates the size of the keel of the glenoid component to be implanted; and
using the rasp to widen the keel receiving hole.

6. The method according to claim 5, wherein said step of selecting an appropriately sized keel drill guide having a drill template which approximates the size of the glenoid component to be implanted and having a through bore which is anteriorly offset from the center of the drill template further comprises the step of selecting a keel drill guide having three through bores which are anteriorly offset from the center of the drill template; said step of drilling through the keel drill guide template to form a keel receiving hole which is anteriorly offset from the center of the recess in the glenoid surface of the scapula further comprises the step of drilling three keel receiving holes; and said step of using the rasp further comprises the step of inserting the rasp in a middle one of the three holes to remove the bone between the three holes to form one broad keel receiving hole.

7. The method according to claim 6 further comprising the steps of:
selecting an appropriately sized glenoid component;
applying bone cement to the medial surface and keel of the glenoid component; and
inserting the keel into the keel receiving hole.

8. The method according to claim 7 further comprising the step of locating the glenoid component such that it is angled inferiorly.

9. The method according to claim 8, wherein said step of locating includes locating the glenoid component such that it is angled approximately 5 degrees inferiorly.

10. A method according to claim 8, wherein said step of locating includes the step of angularly aligning said glenoid component by viewing radiopaque material incorporated therein with the aid of fluoroscopy.

11. A method for shaping the glenoid surface of the scapula for receiving a glenoid prosthesis component, comprising:
drilling a pilot hole in the glenoid surface of the scapula along a central axis of the glenoid;
shaping the surface of the glenoid surface of the scapula using the pilot hole as a guide;
drilling receiving holes in the glenoid surface of the scapula wherein the centers of said guide holes lie along a line parallel to and anteriorly offset from said central axis of the glenoid surface of the scapula; and
connecting the holes to form a slot in the glenoid surface of the scapula.

12. The method as set forth in claim 11, wherein the line connecting the centers of the receiving holes is offset about 2 mm from said central axis.

13. The method as set forth in claim 12, wherein there are three receiving holes.

14. The method as set forth in claim 13, wherein the pilot hole is used to guide the drilling of the receiving holes.

15. The method as set forth in claim 11, wherein said shaping is done by reaming.

16. The method as set forth in claim 15, wherein the reaming step forms a concave glenoid surface in the scapula.

17. The method according to claim 11, wherein said drilling said pilot hole includes selecting an appropriately sized drill guide having a shape approximately said glenoid.

18. The method according to claim 17, wherein said step of selecting an appropriately sized drill guide further comprises selecting a drill guide having an alignment arm for automatically aligning the through hole relative to the scapula at an angle of approximately 65 degrees and further comprises drilling through the through bore of the drill guide to form a pilot hole in the scapula at an angle of approximately 65 degrees relative to the scapula.

19. The method according to claim 11, further including selecting an appropriately sized reaming tool having a reaming surface which approximates the size of the glenoid component to be implanted and having a central guide pin dimensioned to fit in the pilot hole and further comprises selecting an appropriately sized reaming head having a threaded central through bore and attaching the reaming head to a reaming tool having a threaded shaft.

20. The method according to claim 11 further comprising:

after drilling said receiving holes selecting an appropriately sized broach tool having a rasp which approximates the size of a keel of the glenoid component to be implanted; and using the rasp to form the keel receiving hole.

21. The method according to claim 20, wherein said drilling of receiving holes includes selecting an appropriately sized drill guide having a drill template which approximates the size of the glenoid component to be implanted and having a through bore which is anteriorly offset from the center of the drill template and further comprises selecting a drill guide having three through bores which are anteriorly offset from the center of the drill template and drilling through the drill guide template to form receiving holes which are anteriorly offset from the pilot hole and further comprises the step of drilling three keel receiving holes and inserting the rasp in a middle one of the three holes to remove the bone between the three holes to form one broad receiving hole.

22. The method according to claim 21 further comprising the steps of:

selecting an appropriately sized glenoid component having a keel;

applying bone cement to the medial surface and keel of the glenoid component; and inserting the keel into the broad receiving hole.

23. The method according to claim 22 further comprising the step of locating the glenoid component such that it is angled inferiorly.

24. The method according to claim 23, wherein said step of locating includes locating the glenoid component such that it is angled approximately 5 degrees inferiorly.

25. The method according to claim 23, wherein said step of locating includes the step of angularly aligning said glenoid component by viewing radiopaque material incorporated therein with the aid of fluoroscopy.

26. The method of claim 11, wherein the pilot hole is drilled at an anterior/posterior angle.

27. The method of claim 26, wherein the angle is approximately 65°.

28. The method as set forth in claim 26, wherein the receiving holes are drilled at said angle.

* * * * *